United States Patent [19]

Sticklin

[11] Patent Number: 5,160,077
[45] Date of Patent: Nov. 3, 1992

[54] STERILE CORDAGE DISPENSER

[76] Inventor: Scott J. Sticklin, 7650 Birch Bay Drive, Cedar 4, Blaine, Wash. 98230

[21] Appl. No.: 626,627

[22] Filed: Dec. 12, 1990

[51] Int. Cl.⁵ .......................................... B65H 35/06
[52] U.S. Cl. .................................. 225/38; 225/41; 225/42; 225/47; 225/53; 225/80; 225/90
[58] Field of Search .................. 225/41, 15, 42, 53, 225/90, 77, 80, 46, 47, 48, 49, 50, 34, 37, 38, 39; 132/323, 324, 325, 326, 327; 206/406, 408, 409, 411; 242/137, 137.1

[56] References Cited

U.S. PATENT DOCUMENTS

| | | | |
|---|---|---|---|
| 107,786 | 9/1870 | Koch et al. | 242/137 |
| 128,275 | 6/1872 | Baldwin | 242/137 |
| 250,216 | 11/1881 | Dimock | 242/137 |
| D. 257,402 | 10/1980 | Denton et al. | D28/64 |
| D. 266,194 | 9/1982 | Graves | D28/64 |
| 1,279,507 | 9/1918 | Briggs | 132/309 |
| 1,455,673 | 5/1923 | Shalek | 242/138 |
| 1,659,628 | 2/1928 | Greenblatt | 401/155 |
| 1,711,183 | 4/1929 | Smith | 132/309 X |
| 1,981,388 | 11/1934 | Perry | 225/80 |
| 2,172,591 | 6/1938 | Peterson | 132/325 |
| 2,967,651 | 1/1961 | Zackheim et al. | 225/80 |
| 3,018,067 | 1/1962 | Vandervoort | 242/137 |
| 3,112,051 | 11/1963 | Sharpe | 225/38 X |
| 3,284,025 | 11/1966 | Fridolph | 242/137 |
| 3,870,059 | 3/1975 | Bennington | 132/325 |
| 3,870,211 | 3/1975 | Schriever | 225/34 |
| 3,958,768 | 5/1976 | Fairbanks | 206/409 X |
| 4,191,307 | 3/1980 | LeCare, Jr. et al. | 206/409 X |
| 4,327,755 | 5/1982 | Endelson | 132/324 |
| 4,659,028 | 4/1987 | Wren | 206/408 X |
| 4,881,560 | 11/1989 | Blank et al. | 132/324 |

FOREIGN PATENT DOCUMENTS 622060  5/1927  France .

OTHER PUBLICATIONS

A conventional desk top scotch tape dispenser.
Johnson & Johnson Dental floss dispenser.

Primary Examiner—Frank T. Yost
Assistant Examiner—Clark F. Dexter
Attorney, Agent, or Firm—Gregory W. Moravan

[57] ABSTRACT

An apparatus for holding, containing, and dispensing sterile, hygienic cordage, such as dental floss and suture materials. The apparatus comprises: a housing; and cutting and retaining means. The housing has a depression formed therein across which the cordage is placed. The apparatus allows a user to grasp the cordage, withdraw a desired length of cordage, and sever a trailing end thereof without manually touching the apparatus. This reduces the threat of cross-contamination between successive uses and/or users of the apparatus.

5 Claims, 3 Drawing Sheets

STERILE CORDAGE DISPENSER

COPYRIGHT NOTICE

© Copyright 1990 Scott J. Sticklio. All Rights Reserved.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyrights whatsoever.

TECHNICAL FIELD

The present invention relates generally to cordage dispensers; and, more particularly, to sterile or hygienic cordage dispensers used to house, contain, and dispense dental floss and suture materials.

BACKGROUND ART

There has been a long standing need within the dental and medical industries for a convenient, inexpensive, safe, and easily manipulated and assembled apparatus which will house, contain, and dispense sterile strands of cordage, such as dental floss and/or suture materials. To meet this need, a wide variety of devices have been invented. For example, Shalek (U.S. Pat. No. 1,455,673; issued May 15, 1923), Endelson (U.S. Pat. No. 4,327,755; issued May 4, 1982) and Blank et al. (U.S. Pat. No. 4,881,560; issued Nov. 21, 1989) each disclose a different apparatus to dispense dental floss.

Shalek ('673) discloses a permanently mounted dental floss dispenser. One feature of the Shalek ('673) disclosure is a cover which, when in its closed position, acts to protect the floss from dust and handling, but, when moved to its open position, withdraws a length of floss from the container. After withdrawing the desired length of floss from the container, the cover is closed.

Although Shalek ('673) discusses protecting the dental floss from dust and from handling and maintaining it in a sanitary condition, Shalek ('673) does not address the issue of cross-contamination between successive users. For example, if the cover was to become contaminated, such as by catching dust as described in the disclosure or by being exposed to a prior contaminated user, then a successive user would be required to contact and raise the cover to an open position and thereby also become contaminated.

Endelson ('755) and Blank et al. ('560) disclose dental floss dispensers which essentially have a credit card format. The dispensers comprise relatively flat containers having a well therein which is adapted to hold a supply of dental floss. The free end of the dental floss exits from an aperture located in a corner of the flat container and is passed either around cutting means or around a lug and then cutting means. In either case, the dental floss located between the aperture in the flat container and the cutting means lies generally flush against the container.

The design of such devices presents a substantial risk of cross-contamination between successive uses and users. Each user would be constrained to contact the holder and cordage at precisely the same locations on the dispensers in order to grasp and sever a desired length of cordage.

The following patents do not specifically relate to dental floss dispensers. Instead, the following patents relate to holders and dispensers for multiple spools of sewing thread, cotton, and silk: Koch et al. (U.S. Pat. No. 107,786; issued Sep. 27, 1870); Baldwin (U.S. Pat. No. 128,275; issued Jun. 25, 1872); Dimock (U.S. Pat. No. 250,216; issued Nov. 29, 1881); Vandervoort (U.S. Pat. No. 3,018,067; issued Jan. 23, 1962); and Fridolph (U.S. Pat. No. 3,284,025; issued Nov. 8, 1966). Since these disclosures were not specifically directed to dental floss dispensers, the patentees apparently were not concerned with cross-contamination and made no provision therefor. If any of these devices were used to contain sterilized dental floss, the problem of cross-contamination would not be resolved.

All of the foregoing devices subject successive users to cross-contamination. Use of light, portable, and easily manipulated housings require, by their very nature, that the user contact and hold the very same housing that is used to protect the contained dental floss against contamination. The contaminants and foreign elements which are captured by the exterior surfaces of the housing are thus passed to the hands and fingers of the user. The very nature of the dispenser construction ensures that each person using the dispenser will, of necessity, come into contact with the cutting mechanism and outer surfaces of the dispenser, thereby subjecting successive users to cross-contamination.

Furthermore, the close proximity between the retained end of the thread and the housing increases the likelihood that contaminants which contact the housing will also contact either the thread or the fingers of a successive user. This in turn increases the likelihood that complications after use of the device may arise due to the presence of dangerous bacteria, viruses, or other substances. This is particularly true when infectious substances which produce such illnesses such as hepatitis and acquired immune deficiency syndrome (AIDS) are present.

Another disadvantage of using small, hand-held dispensers is that both hands are required to obtain a desired length of cordage. Many times a dentist and/or surgeon has at least one hand occupied when he or she desires to obtain a length of sterile cordage. Where a hand-held container is used, either the doctor must remove his or her hands to accomplish the task of obtaining and severing a length of cordage, or the services of an assistant must be obtained. Thus, such devices are often difficult and/or inconvenient to use. This is particularly true when the doctor is in a dangerous or awkward position or stage of the operation.

The inventor believes the listed patents and known prior art taken alone or in combination neither anticipate nor render obvious the present invention. These citations do not constitute an admission that such disclosures are relevant or material to the present claims. Rather, these citations relate only to the general field of the disclosure and are cited as constituting the closest art of which the inventor is aware.

DISCLOSURE OF INVENTION

The present invention is a hygienic cordage dispenser which substantially precludes the danger of cross-contamination between successive uses and/or users. More particularly, the present invention is a cordage dispenser that may be used to house, contain, and dispense sterile, hygienic dental floss and suture materials without exposure to a threat of cross-contamination between successive users. The present invention is inexpensive and economical to manufacture, and is easily constructed and assembled. The invention is extremely simple to use, requires minimal time, intelligence and dexterity to assemble and to manipulate. The invention is both functional and aesthetically pleasing. In addition to having these positive qualities, the present invention overcomes and eliminates all of the previously mentioned disadvantages and does not expose users to the aforementioned dangers.

It is believed that one of the inventive features of the present invention resides in the configuration of the cordage dispenser, wherein a hygienic depression is provided between a location where the cordage exits the housing and a location where the cordage is cut and retained.

To achieve these general and specific objectives the present invention comprises an apparatus for holding, containing, and dispensing sterile cordage, such as dental floss and/or suture materials. The apparatus generally comprises: a base member; a cover; and means for cutting and retaining one or more strands of cordage.

The base member and cover define a housing, enclosure, or compartment which is capable of holding and retaining one or more spools of cordage. For example, one spool of cordage may comprise a spool of waxed dental floss and the other spool may be unwaxed dental floss.

The base member has a floor and at least one side wall. The floor is generally flat. The floor and side wall are integrally formed with one another, with the side wall extending outwardly away from the floor. The base member also has one or more stanchions therein which project outwardly from the floor to support one or more bobbins or the cordage. For added strength, the floor, side wall, and stanchion of the base member may be formed integrally with one another.

The side wall of the base member also has means for securing the cover thereto. The securing means may comprise a peripheral rim located around an outer edge of the side wall of the base member. The cover then has a complementary, corresponding ridge which engages and interlocks with the rim to removably secure the cover to the base member.

To assure proper aligned engagement, the base member and the cover may further comprise means for aligning the base member and the cover. For example, the base member may be provided with a flange which extends outwardly from the side wall. The cover has a corresponding notch which, when engaged with the base member, mates and interlocks with the flange.

The cover may also be provided with one or more recess or notch to facilitate easy detachment from the base member.

Furthermore, the apparatus may be provided with means for rigidly and/or permanently affixing the base member to a stationary support surface. For example, such securing means may comprise a screw, bolt, or adhesive which secures the base member to the support surface.

The cover generally defines a housing for one or more spools of the cordage. The cover is capable of being superposed and secured to the base member to form an enclosure. The cover also has one or more stanchions which urge the spool of cordage into proper position and alignment for rotation within the enclosure. Although the preferred embodiment is designed to accommodate cordage stored in a coiled form, other forms such as spiral, helical, or serpentine can also be used.

The cover may be made of transparent, translucent, and/or opaque material.

The cover has at least one aperture through which the cordage may be passed from within the enclosure to an exterior of the housing. In the preferred embodiment the aperture comprises an annular slot.

The cover is also contoured to have a pronounced hygienic depression therein. In the preferred embodiment, the cover is designed such that a hygienic depression is located between two spools of cordage held within the enclosure. The cordage on the spools passes outwardly from within the enclosure through respective apertures in the cover. The cordage then passes over the hygienic depression to engaged the cutting and retaining means.

The apparatus is also provide with means for cutting and retaining one or more strands of the cordage. For example, the cutting and retaining means may comprise a metal plate having one or more partially raised, outwardly projecting tabs punched or cut therein. The tabs have a sharp intersection with a remaining portion of the metal plate. When a strand of cordage is urged therebetween the sharp intersection severs the strand and retains the remaining severed end of the strand.

During use, the cordage exits the enclosure through the aperture, and spans across the depression. The cordage then engages and is retained by the cutting and retaining means. The span of the cordage across the depression, and the access room provided by the contour of the depression enables a user to grasp the spanned cordage without contacting any portion of the apparatus. Thus, the danger of cross-contamination between successive uses and/or users is reduced.

If a plurality of the spools are used, the cover may have a plurality of corresponding, spaced apertures and cutting and retaining means. Once each strand of cordage is passed through their respective aperture, the strands will assume a spaced relationship with to each other. Thus configured, a user may simply grasp whichever strand of cordage he or she desires within the region of the hygienic depression without having to touch any portion of the dispenser. This facilitates easy access and selection of the desired cordage.

The leading end of the cordage is disengaged from the cutting and retaining means. A desired length of cordage is dispensed, and a trailing end of the cordage is urged into engagement with the cutting and retaining means, thereby severing the desired length from the spool supply. By providing the cover with a hygienic depression, the risk of cross-contamination between successive users is reduced.

These and other objectives and advantages of the present invention will become more readily apparent upon reading the following disclosure and referring to the attached drawings.

Figure 1:
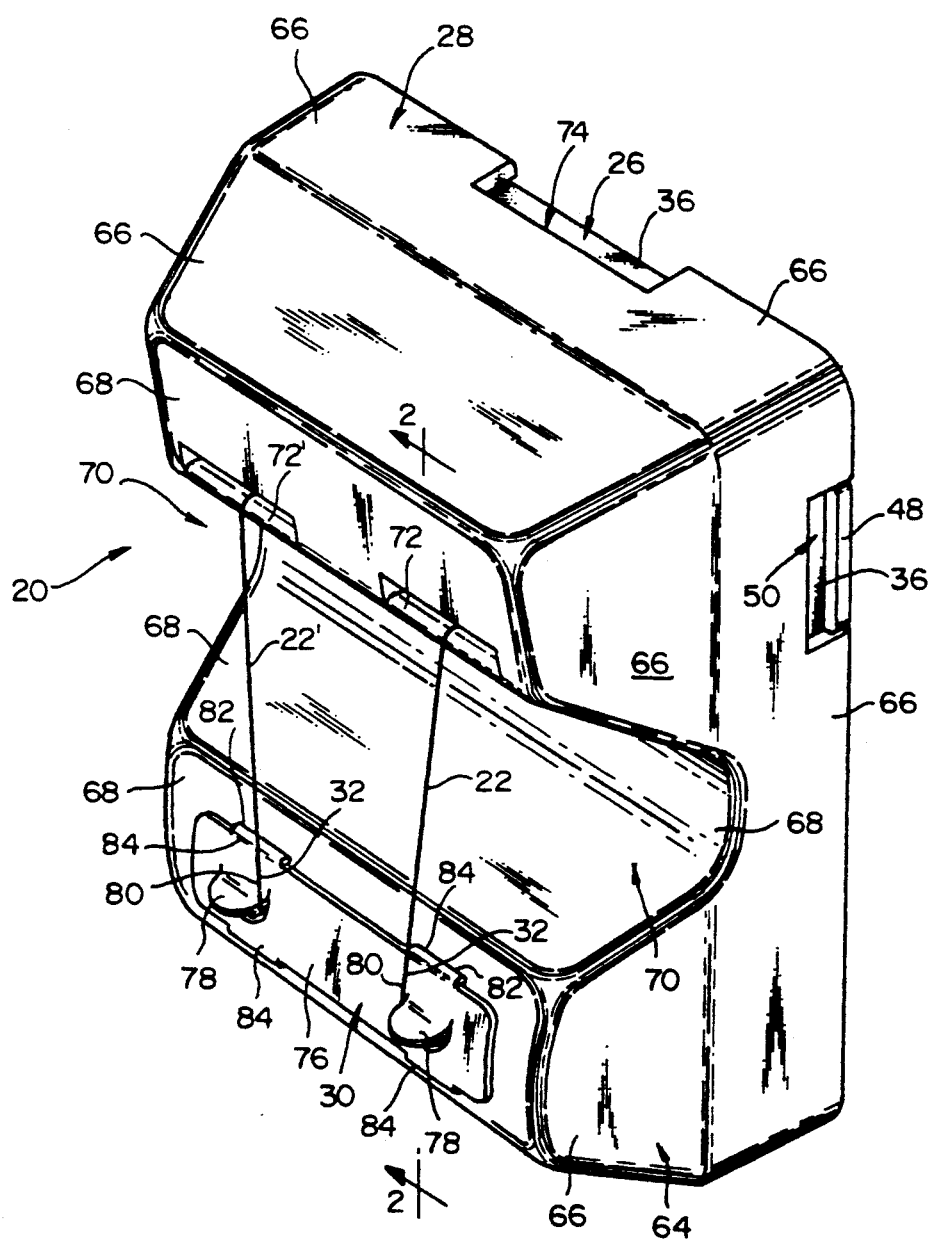
FIG. 1 is an isometric view of a preferred embodiment of the invention.

One should understand that the drawings are not necessarily to scale and the elements are sometimes illustrated by graphic symbols, phantom lines, diagrammatic representations, and fragmentary views. In certain instances, the inventor may have omitted details which are not necessary for an understanding of the present invention or which render other details difficult to perceive.

BEST MODE FOR CARRYING OUT THE INVENTION

Referring to FIGS. 1 through 4 in the drawings, wherein like numerals indicate like parts, the present invention is an apparatus 20 for holding, containing, and dispensing sterile, hygienic dental floss 22 and/or suture material which precludes the danger of cross-contamination between successive uses and/or users. Furthermore, apparatus 20 is intended to be fixedly mounted to an underlying support surface 24 located at work stations in dental offices or at fixed points in a users' home near where the users brush and floss their teeth.

In its broadest aspect, however, the present invention is equally applicable to both stationary and to portable dental floss dispensers.

In the illustrated embodiment, apparatus 20 comprises: a base member 26; a cover 28; and means 30 for cutting and retaining one or more leading ends 32 of floss 22.

Base Member

Figure 2:
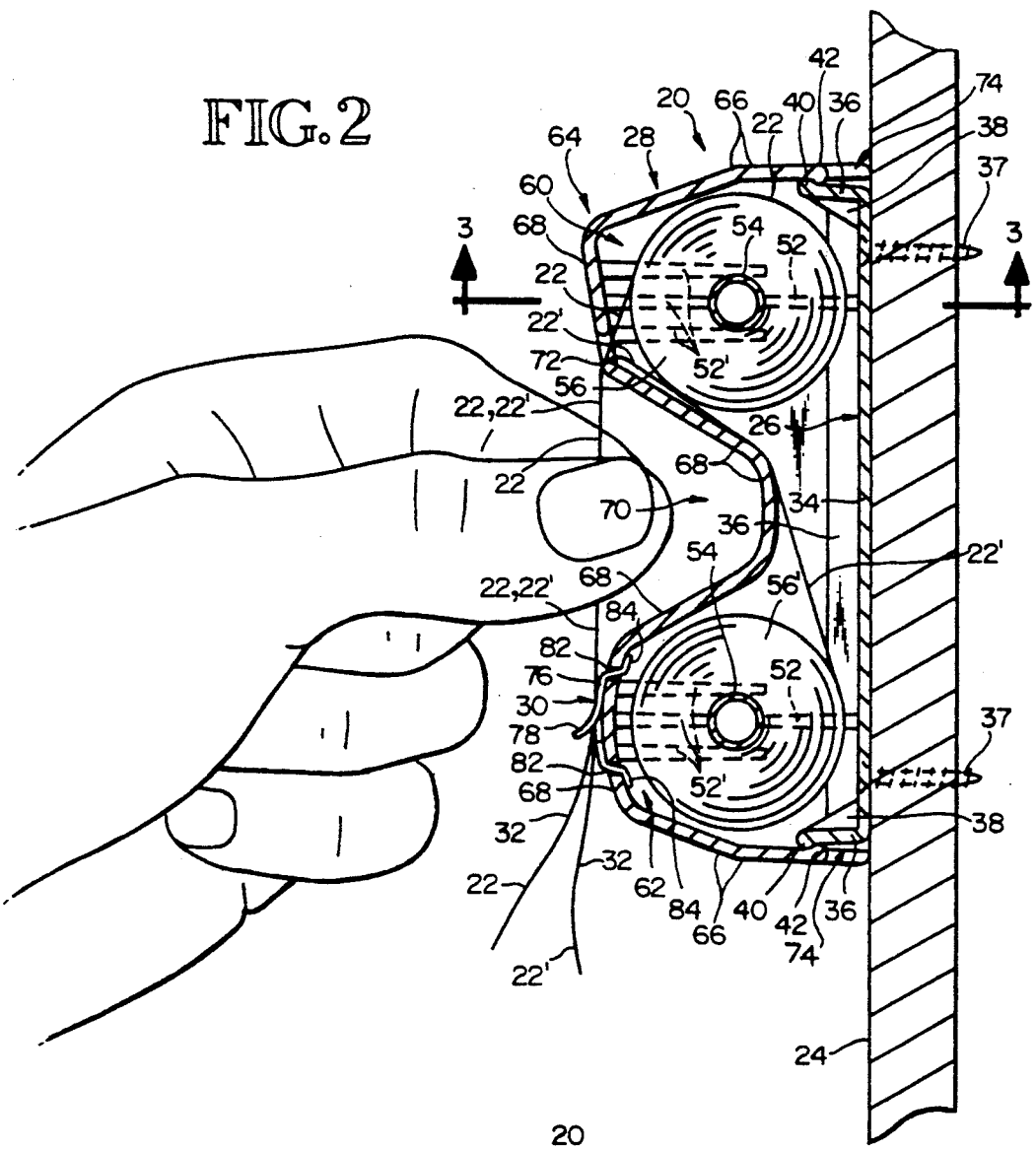
FIG. 2 is a cross-sectional, side-elevational view of the invention as seen along a plane defined by line 2—2 in FIG. 1, illustrating how the leading end of the cordage may be grasped without contacting any surface of the housing.
Figure 3:
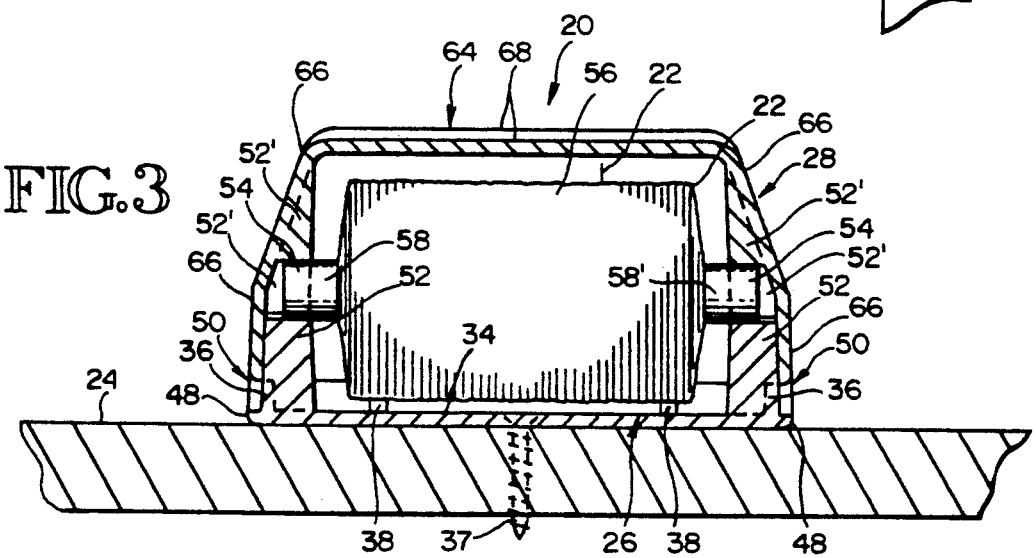
FIG. 3 is a cross-sectional, end-elevational view of the invention as seen along a plane defined by line 3—3 in FIG. 2, illustrating how the spool of cordage may be supported within the enclosure of the housing.

Base member 26 has a floor 34 and generally tangential, outwardly projecting side walls 36 which together define a generally shallow rectangular tray or well. Floor 34 is generally flat and is designed to be juxtaposed against and secured to underlying support surface 24. Floor 34 may be secured to support surface 24 by any adequate securing means, such as by use of one or more screws and/or bolts, adhesive, clamps, hook and loop fasteners, or the like. FIGS. 2 and 3 illustrate use of countersunk screws 37 which pass through corresponding through bores located in base member 26 and engage and support structure 24.

Alternatively, base member 26 may be secured to support surface 24 by means of applying a series of double sided adhesive strips (not shown) on base member 26, and then urging the adhesive strips into contact against a wall or other structure. This method enables essentially permanent securement of the device at the desired location.

Support surface 24 may comprise any adequate support surface such as a tray, cart, table, counter top, wall, cabinet, or the similar supporting structure.

Side walls 36 are located around the periphery of floor 34 and extend outwardly or tangentially away from support structure 24. Side walls 36 may be braced in position, to resist rotational movement, by means of using one or more braces 38 which are secured between side walls 36 and floor 34.

One or more of side walls 36 are provided with means of securing cover 28 thereto. As best illustrated in FIG. 2, such securing means may comprise a peripheral rim 40 or lip located around an outer edge of side walls 36.

When cover 28 is superposed and secured to base member 26, peripheral rim 40 removably engages complementary, corresponding ridges 42 located on the interior surfaces of cover 28. The frictional engagement between rim 40 and ridges 42 causes cover 28 to be removably secured to base member 26.

In an alternative embodiment, cover 28 may be permanently secured or bonded to base member 26. For example permanent bonding may be accomplished by using a suitable adhesive or by using heat and pressure to effect thermal bonding of thermoplastic portions.

Base member 26 and cover 28 may be provided with means for aligning these two elements into proper engagement with one another. As best shown in FIG. 1, proper engagement may be accomplished by providing base member 26 with a flange 48 which extends outwardly from side walls 36. Cover 28 is provided with a corresponding notch 50 which, when engaged with base member 26, mates with flange 48.

Base member 26 further comprises one or more stanchions 52 which project outwardly from floor 34. Stanchions 52 may be secured to and supported by adjacent side walls 36. The purpose of stanchions 52 is to serve as a support for one or more bobbins 54 or spool pins.

Floor 34, side walls 36, braces 38, rims 40, flanges 48, and stanchions 52 of base member 26 may be formed integrally with one another, as may be achieved by using an injection or vacuum molding process, or they may be independently formed and then secured to each other as described above.

Floss 22 may comprise any cordage which is intended to be protected from contamination. For example, floss 22 may comprise waxed or unwaxed dental floss, flavored or unflavored dental floss, dental and/or surgical suture material, thread, optical fibers, wire, or the like.

Typically, such cordage or floss 22 is wrapped around a bobbin 54 to form a spool 56. As best seen in FIG. 3, in the preferred embodiment of the invention, floss 22 is wrapped around bobbin 54 in such a manner as to not contact or interfere with the respective ends 58 and 58' of bobbin 54. Bobbins 54 may comprise solid rods, or hollow tubes as shown in FIG. 2.

Cover

Cover 28 comprises the primary protective housing for one or more spools 56 of floss 22. Although this invention may be used to protect a single spool 56 of floss 22, it is intended to accommodate two or more, spools 56 of floss 22. For example, apparatus 20 may be used to hold, retain, and dispense waxed and unwaxed floss 22, or flavored and unflavored floss 22, or any combination thereof. It is not necessary that apparatus 20 be designed to include two spools 56 of floss 22. Thus, apparatus 20 might include one, two, or more spools 56.

Figure 4:
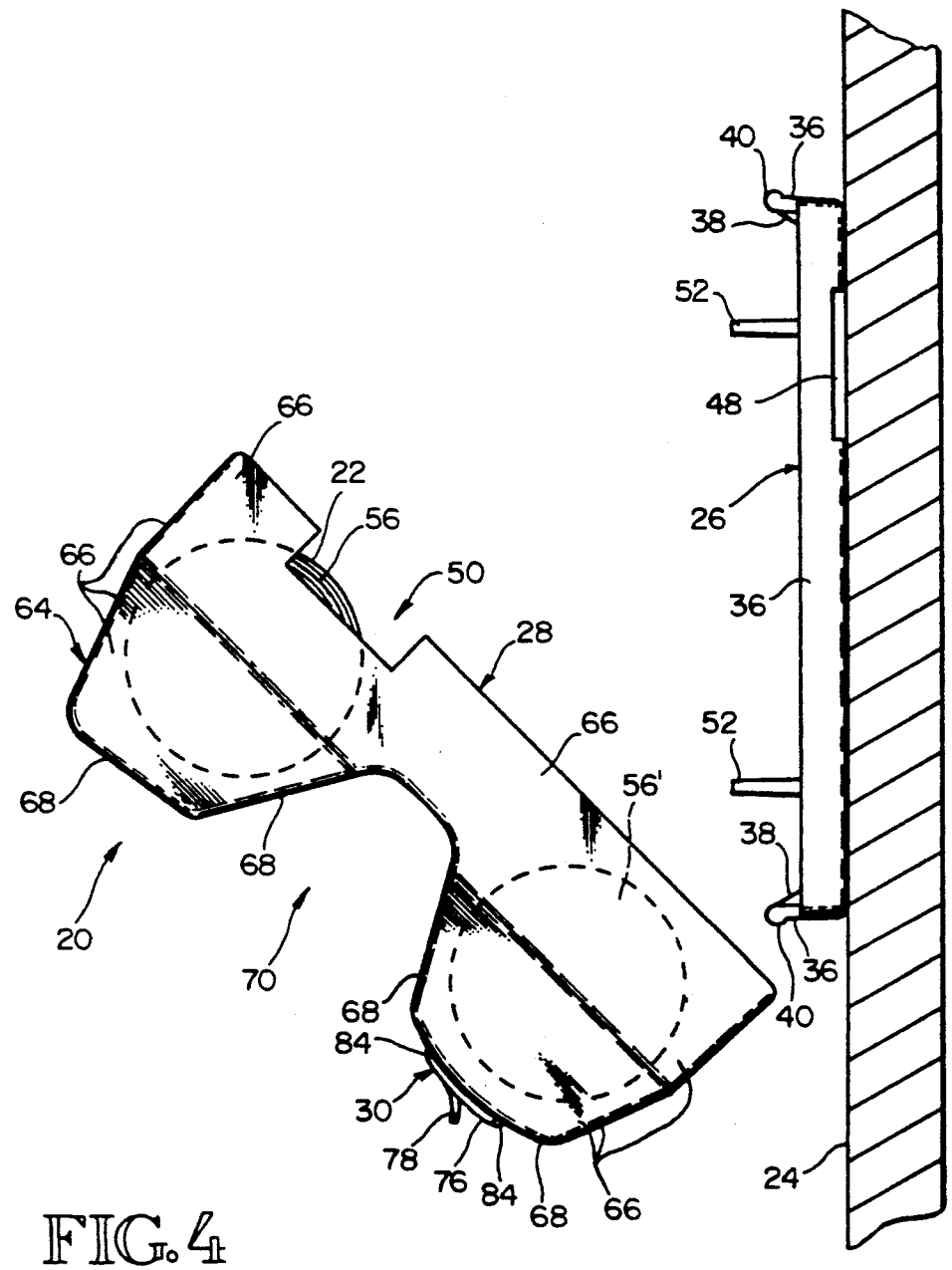
FIG. 4 is an exploded, side-elevational view of the invention illustrating the separability between the upper portion and lower portion of the housing. The spools of cordage are generally illustrated in phantom lines.

In the preferred embodiment, as best seen in FIGS. 2 and 4, cover 28 comprises a housing which generally defines the boundaries of two wells or compartments 60 and 62. Compartment 60 is designed to hold and retain spool 56 of floss 22. Compartment 60' is designed to hold and retain spool 56' of floss 22'. The size, dimensions, and configuration of compartments 60 and 62 ar largely dependent upon the respective sizes and dimensions of spools 56 and 56'.

In the preferred embodiment, cover 28 comprises an integral, unitary housing 64 generally having side walls 66 and an upper surface 68. When attached to base member 26, side walls 66 and upper surface 68 serve to encapsulate spools 56 and 56' within housing 64, thereby sealing the enclosure to maintain the sterile condition of floss 22 and 22'. As stated above, the interior surface of side walls 66 have been provided with ridges 42 which engage and interlock with rim 40.

In an alternative embodiment of the invention, instead of or in addition to having ridges 42 and rims 40, cover 28 could be hingedly connected to base member 26 at one end, and latched at an opposite end. This embodiment is not illustrated.

Cover 28 is contoured to provide a pronounced hygienic depression 70 adjacent to where floss 22 and 22' is grasped by the user so that the user may grasp floss 22 and 22' without touching any portion of the dispenser or apparatus 20, thereby reducing the risk of cross-contamination between successive users. It is important to note that side walls 66 and upper surface 68 are provided with depression 70 which is located generally between compartments 60 and 62. Depression 70 has sufficient depth thereto that the fingers of a user may enter therein without necessarily coming into contact with cover 28.

The portion of upper surface 68 which defines compartment 60 is provided with at least one aperture 72 through which the leading end 32 of floss 22 may pass.

As illustrated in FIG. 2, the primary supply of floss 22 on spool 56 is held and retained within an enclosure defined by the joined cover 28 and base member 26. It is important that floss 22 be able to be removed from spool 56. Therefore, in the preferred embodiment, spool 56 is held in place by respective stanchions 52 and 52' in such a manner that spool 56 may freely rotate about an axis defined by the longitudinal axis of bobbin 54. Stanchions 52' are formed within side walls 66 of cover 28 such that they are generally above or beside stanchion 52. Stanchions 52' are provided in both compartments 60 and 62. The purpose of stanchions 52' is to retain ends 58 and 58' of bobbins 54 and 54' in proper position and alignment such that spools 56 and 56' may freely rotate, and floss 22 and 22' may be freely dispensed therefrom.

The present invention may still be used if the supply of floss 22 is stored in a spiral, helical, or serpentine coil, as long as lengths thereof are easily dispensed therefrom.

In the preferred embodiment, floss 22 on spool 56 is rotationally secured within compartment 60 of the enclosure. Leading end 32 of floss 22 passes outwardly from within the enclosure through aperture 72. Leading end 32 of floss 22 is then urged to span across and over depression 70 and engage cutting and retaining means 30.

Similarly, the supply of floss 22' on spool 56' is rotationally secured within compartment 62. Leading end 32 of floss 22' extends beneath depression 70 of cover 28 and is urged outward from within the enclosure through either aperture 72 or through a separate aperture 72'. The leading end 32 of floss 22' is similarly urged to span across and over depression 70 and engage cutting and retaining means 30. Apertures 72 and 72' may comprise a simple perforation, an orifice, or an annular slot or opening through which floss 22 and 22' may be passed for dispensing.

FIGS. 1 and 2 particularly illustrate that floss 22 and 22' exit apertures 72 and 72' and extend across the hygienic depression 70 to terminate at cutting and retaining means 30. Thus configured, a user may easily grasp one or the other, or both, of leading ends 32 of floss 22 or 22' within the region of depression 70 wherein it is unnecessary to touch any portion of apparatus 20. Consequently, the risk of cross-contamination between successive uses and/or users is reduced.

When spool 56 or 56' of floss 22 or 22' is spent, the user may simply remove cover 28 from attachment to base member 26, replace the spent spool, rethread the leading end 32 of floss 22 or 22' through the appropriate aperture 72 or 72', and then resecure cover 28 to base member 26. Once the leading end 32 is passed around cutting and retaining means 30 and thereby severed, apparatus 20 is again ready for use.

Cover 28 may be provided with a recess 74 or slot in one or more side walls 66 to facilitate easy removal of cover 28 from attachment to base member 26. As seen in FIG. 1, the user may easily place his or her finger tips into recess 74 or into notches 50 to gain greater leverage or frictional contact to remove cover 28 from base member 26.

Side walls 66, upper surface 68, ridges 42, and stanchions 52' of cover 28 may be formed integrally with one another, as may be achieved by using an injection or vacuum molding process, or they may be independently formed and then secured to each other as described above.

Cover 28 may be made of transparent material to reveal underlying spools 56 and 56' and show the extend to which floss 22 and 22' are depleted. Alternatively, cover 28 may be made of an opaque plastic material which may be printed upon or be embossed to carry identification, advertising or promotional material as are commonly used within the dental and medical industries.

Both base member 26 and cover 28 may be fabricated of synthetic plastic material, such as polyvinyl chloride, or of other thermoplastic material, metal, or sealed wood.

CUTTING AND RETAINING MEANS

Cutting and retaining means 30 may comprise any apparatus or device which is capable of engaging and severing a length of floss 22 or 22' from the remaining supply of floss 22 and 22' on spools 56 or 56'. It is important, however, that once severed, floss 22 and 22' span across the depression 70 formed in cover 28, and thus place floss 22 and 22' in an accessible position for severing additional lengths therefrom. Several cutting and retaining means 30 have been disclosed in the prior art, and any one of them could serve the aforesaid function.

In the preferred embodiment, cutting and retaining means 30 comprises a metal plate 76 having one or more partially raised, outwardly projecting U- or V-shaped tabs 78 punched or cut therein. Leading end 32 may be pulled, drawing a desired length of floss 22 or 22' from apparatus 20. A trailing end 80 is then passed into engagement and contact with a sharp intersection located between tabs 78 and the remaining portion of metal plate 76. A slight jerk on leading end 32 will cause trailing end 80 of floss 22 or 22' to sever at the juncture, and trailing end 80 will become retained between tab 78 and metal plate 76, thus becoming a new leading end 32.

By utilizing a separate aperture 72 and tab 78 for each of several spools 56 and 56', each leading end 32 is maintained in a spaced relationship with adjacent cordage. This simplifies the selection and removal of the cordage from the selected spool.

As best illustrated in FIG. 2, metal plate 76 is secured to upper surface 68 by first providing upper surface 68 with one or more annular through slots 82. Metal plate 76 is provided with corresponding downwardly projecting tabs 84 which pass through slots 82 and are bent to securely engage and attach metal plate 76 to cover 28. Other means of securing metal plate 76 to cover 28 may alternatively be used.

Method of Use

To use apparatus 20, one merely disengages leading end 32 of floss 22 or 22' from tab 78, and pulls out a suitable length of floss 22 or 22' from within the enclosure. The trailing end 80 of which is then inserted beneath tab 78, and by applying suitable stress to floss 22 or 22' the raw, sharp edge of tab 78 functions to sever the floss while retaining the trailing end 80. Since apparatus 20 is secured to support surface 24, apparatus 20 need not be manually held in place during the dispensing process. Floss 22 and 22' may thus be removed by being grasped, pulled, and severed by the actions of a single hand, and if grasped near hygienic depression 70 no contact with apparatus 20 occurs.

The means and construction disclosed herein are by way of example and comprise primarily the preferred form of putting the invention into effect. Although the drawings depict a preferred embodiment of the invention, other embodiments have been described within the preceding text. One skilled in the art will appreciate that the disclosed device may have a wide variety of shapes and configurations. Additionally, persons skilled in the art to which the invention pertains might consider the foregoing teachings in making various modifications, other embodiments, and alternative forms of the invention.

It is, therefore, to be understood that the invention is not limited to the particular embodiment or specific features shown herein. To the contrary, the inventor claims the invention in all of its forms, including all modifications, equivalents, and alternative embodiments which fall within the legitimate and valid scope of the appended claims, appropriately interpreted under the Doctrine of Equivalents.

INDUSTRIAL APPLICABILITY

The present invention comprises simple, reliable, easily used, and inexpensively manufactured apparatus and methods for holding, containing, and dispensing sterile, hygienic cordage, such as dental floss and suture materials, without exposing successive uses and/or users to a danger of cross-contamination. This invention allows a user to grasp a leading end of the stored cordage, withdraw a desired length, and sever a trailing end thereof with a single hand, without manually touching the apparatus. Consequently, this invention is ideal for use in environments where the elimination of cross-contamination is important or imperative, such as in dental and/or surgical environments. The present invention is equally effective within a home environment, and may be used by both children and adults. The apparatus and methods taught herein not only increase the speed and ease of dispensing sterile cordage, they also eliminate the exposure of multiple uses and/or users to the dangers previously associated with cordage dispensing devices.

What is claimed is:

1. A holding and dispensing apparatus for holding and dispensing cordage from at least a first and a second cordage supply; wherein said holding and dispensing apparatus comprises: a base means; a cover means secured to said base means; an aperture means for providing at least one aperture in said cover means; a first and a second cutting and retaining means for selectively cutting and retaining said cordage from said first and second cordage supplies, respectively, during use of said holding and dispensing apparatus; and a mounting means secured to said base means for mounting said base means to a support surface; wherein said base means and said cover means are for forming a housing means for housing said first and second cordage supplies; wherein said housing means comprises a first and a second compartment means; wherein said first and second compartment means are for receiving said first and second cordage supplies, respectively, during use of said holding and dispensing apparatus; wherein said first and second compartment means are spaced apart from each other; wherein said cover means is also for forming an elongated, deep hygienic depression means; wherein said elongated, deep hygienic depression means is located between said first and second compartment means; wherein said aperture means comprises a part of said first compartment means; wherein said first and second cutting and retaining means are secured to an outer surface of said second compartment means; wherein, during use of said holding and dispensing apparatus, said cordage from said first cordage supply extends from said first cordage supply, out of said housing means through said aperture means, and over said elongated, deep hygienic depression means to said first cutting and retaining means; wherein, during use of said holding and dispensing apparatus, said cordage from said second cordage supply extends from said second cordage supply, under said elongated, deep hygienic depression means, out of said housing means through said aperture means, and over said elongated, deep hygienic depression means to said second cutting and retaining means; wherein, during use of said holding and dispensing apparatus, said first and second cordage supplies have a first and a second cordage gripping portion, respectively, which extend between said aperture means and said first and second cutting and retaining means, respectively; wherein said elongated, deep hygienic depression means is for permitting said user to easily grasp either of said first and second cordage gripping portions without touching said elongated, deep hygienic depression means, in order to help to avoid undesirable cross contamination of said first and second cordage gripping portions with said elongated, deep hygienic depression means, and with said user's fingers; wherein, during use of said holding and dispensing apparatus, said holding and dispensing apparatus is mounted to said support surface with said aperture means located above said first and second cutting and retaining means, and with said first and second cordage gripping portions oriented at least substantially vertically; and wherein said aperture means and said cutting and retaining means are also for widely separating said first and second cordage gripping portions a distance sufficient to enable a user's fingers to easily grasp one of said first and second cordage gripping portions without said user's fingers touching the other of said first and second cordage gripping portions, in order to help to avoid undesirable cross contamination of said first and second cordage gripping portions with each other, and with said user's fingers.

2. A holding and dispensing apparatus for holding and dispensing cordage from at least a first and a second cordage supply; wherein said holding and dispensing apparatus comprises: a base means; a cover means secured to said base means; an aperture means for providing at least one aperture in said cover means; and a first and a second cutting and retaining means for selectively cutting and retaining said cordage from said first and second cordage supplies, respectively, during use of said holding and dispensing apparatus; wherein said base means and said cover means are for forming a housing means for housing said first and second cordage supplies; wherein said housing means comprises a first and a second compartment means; wherein said first and second compartment means are for receiving said first and second cordage supplies, respectively, during use of said holding and dispensing apparatus; wherein said first and second compartment means are spaced apart from each other; wherein said cover means is also for forming an elongated, deep hygienic depression means; wherein said elongated, deep hygienic depression means is located between said first and second compartment means; wherein said aperture means comprises a part of said first compartment means, wherein said first and second cutting and retaining means are secured to an outer surface of said second compartment means; wherein, during use of said holding and dispensing apparatus, said cordage from said first and second cordage supplies extend from said first and second cordage supplies, out of said housing means through said aperture means, and over said elongated, deep hygienic depression means to said first and second cutting and retaining means, respectively; wherein, during use of said holding and dispensing apparatus, said first and second cordage supplies have a first and a second cordage gripping portion, respectively, which extend between said aperture means and said first and second cutting and retaining means, respectively; and wherein said elongated, deep hygienic depression means is for permitting said user to easily grasp either of said first and second cordage gripping portions without touching said elongated, deep hygienic depression means, in order to help to avoid undesirable cross contamination of said first and second cordage gripping portions with said elongated, deep hygienic depression means, and with said user's fingers.

3. The holding and dispensing apparatus according to claim 2, wherein said holding and dispensing apparatus further comprises: a mounting means secured to said base means for mounting said base means to a support surface; and wherein, during use of said holding and dispensing apparatus, said holding and dispensing apparatus is mounted to said support surface with said aperture means located above said first and second cutting and retaining means, and with said first and second cordage gripping portions oriented at least substantially vertically.

4. The holding and dispensing apparatus according to claim 2, wherein said aperture means and said cutting and retaining means are also for widely separating said first and second cordage gripping portions a distance sufficient to enable a user's fingers to easily grasp one of said first and second cordage gripping portions without said user's fingers touching the other of said first and second cordage gripping portions, in order to help to avoid undesirable cross contamination of said first and second cordage gripping portions with each other, and with said user's fingers.

5. The holding and dispensing apparatus according to claim 2, wherein during use of said holding and dispensing apparatus, said cordage from said second cordage supply extends from said second cordage supply, under said elongated, deep hygienic depression means, out of said housing means through said aperture means, and over said elongated, deep hygienic depression means to said second cutting and retaining means.

* * * * *